United States Patent
Salamone et al.

(10) Patent No.: US 6,852,793 B2
(45) Date of Patent: Feb. 8, 2005

(54) LOW WATER CONTENT, HIGH REFRACTIVE INDEX, FLEXIBLE, POLYMERIC COMPOSITIONS

(75) Inventors: Joseph C. Salamone, Boca Raton, FL (US); Jay F. Kunzler, Canadaigua, NY (US); Richard M. Ozark, Solvay, NY (US); David E. Seelye, North Chili, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/175,715

(22) Filed: Jun. 19, 2002

(65) Prior Publication Data

US 2003/0236375 A1 Dec. 25, 2003

(51) Int. Cl.$^7$ .................. C08F 122/10; C08F 212/08
(52) U.S. Cl. .................. 524/560; 524/359; 526/307.5; 526/307.7; 526/320; 623/6.11; 523/106; 351/160 H
(58) Field of Search ................ 524/560, 359; 526/307.5, 307.7, 320; 623/6.11; 523/106; 351/160 H

(56) References Cited

U.S. PATENT DOCUMENTS

| | | | |
|---|---|---|---|
| 3,996,187 A | 12/1976 | Travnicek | 260/37 |
| 3,996,189 A | 12/1976 | Travnicek | 260/37 |
| 4,190,693 A | 2/1980 | Martorano et al. | 428/209 |
| 4,418,165 A | 11/1983 | Polmanteer et al. | 523/210 |
| 4,647,282 A | 3/1987 | Fedorov et al. | 623/4 |
| 4,868,251 A | 9/1989 | Reich et al. | 525/479 |
| 5,512,609 A | 4/1996 | Yang | 523/107 |
| 5,623,029 A | 4/1997 | Yang | 525/478 |
| 6,245,106 B1 | 6/2001 | Makker et al. | 623/5.16 |
| 6,277,940 B1 * | 8/2001 | Niwa et al. | 526/328.5 |
| 6,326,448 B1 | 12/2001 | Ojio et al. | 526/259 |
| 6,465,588 B1 * | 10/2002 | Li | 526/258 |
| 6,555,030 B1 | 4/2003 | Weinschenk, III | 264/1.7 |

FOREIGN PATENT DOCUMENTS

WO   WO 01/81075 A2   1/2001

* cited by examiner

Primary Examiner—Tatyana Zalukaeva
Assistant Examiner—Satya B Sastri
(74) Attorney, Agent, or Firm—Rita D. Vacca

(57) ABSTRACT

Optically transparent, relatively high refractive index polymeric compositions and ophthalmic devices such as intraocular lenses and corneal inlays made therefrom are described herein. The preferred polymeric compositions are produced through the polymerization of one or more copolymers with one or more hydrophilic monomers and optionally one or more aromatic-based monomers, hydrophobic monomers or a combination thereof.

30 Claims, No Drawings

LOW WATER CONTENT, HIGH REFRACTIVE INDEX, FLEXIBLE, POLYMERIC COMPOSITIONS

FIELD OF THE INVENTION

The present invention relates to polymeric compositions useful in the manufacture of biocompatible medical devices. More particularly, the present invention relates to copolymers capable of polymerization to form polymeric compositions having desirable physical characteristics and refractive indices useful in the manufacture of ophthalmic devices.

BACKGROUND OF THE INVENTION

Since the 1940's ophthalmic devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. In general, the materials of current commercial IOLs fall into one of three general categories: silicones, hydrophilic acrylics and hydrophobic acrylics.

In general, high water content hydrophilic acrylics, or "hydrogels," have relatively low refractive indices, making them less desirable than other materials with respect to minimal incision size. Low refractive index materials require a thicker IOL optic portion to achieve a given refractive power. Silicone materials may have a higher refractive index than high-water content hydrogels, but tend to unfold explosively after being placed in the eye in a folded position. Explosive unfolding can potentially damage the corneal endothelium and/or rupture the natural lens capsule and associated zonules. Low glass transition temperature hydrophobic acrylic materials are desirable because they typically have a high refractive index and unfold more slowly and more controllably than silicone materials. Unfortunately, low glass transition temperature hydrophobic acrylic materials, which contain little or no water initially, may absorb pockets of water in vivo causing light reflections or "glistenings." Furthermore, it may be difficult to achieve ideal folding and unfolding characteristics due to the temperature sensitivity of some acrylic polymers.

Because of the noted shortcomings of current polymeric materials available for use in the manufacture of ophthalmic implants, there is a need for stable, biocompatible polymeric materials having desirable physical characteristics and refractive indices.

SUMMARY OF THE INVENTION

Soft, foldable, high refractive index, high elongation polymeric compositions of the present invention having a water content greater than 4.5 percent to avoid water vacoule formations or "glistenings" in vivo are produced through the polymerization of one or more copolymers with one or more hydrophilic monomers. Such suitable copolymers are produced by combining two or more $C_{1-10}$ alkyl methacrylate, $C_{1-10}$ alkyl acrylate, $C_{6-40}$ arylalkyl acrylate, or $C_{6-40}$ arylalkyl methacrylate monomers. The polymeric compositions produced from such copolymers and hydrophilic monomer(s) have ideal physical properties for the manufacture of ophthalmic devices. The polymeric compositions of the present invention are transparent, flexible, of relatively high strength for durability during surgical manipulations, of relatively high elongation, of relatively high refractive index and are biocompatible. The subject polymeric compositions are particularly well suited for use as intraocular lens (IOLs) implants, contact lenses, keratoprostheses, corneal rings, corneal inlays and the like.

Accordingly, it is an object of the present invention to provide transparent, flexible, polymeric compositions having desirable physical characteristics for the manufacture of ophthalmic devices.

Another object of the present invention is to provide polymeric compositions of relatively high refractive index.

Another object of the present invention is to provide polymeric compositions suitable for use in the manufacture of intraocular lens implants.

Another object of the present invention is to provide polymeric compositions that are biocompatible.

Another object of the present invention is to provide polymeric compositions are flexible with desirable memory properties.

Still another object of the present invention is to provide polymeric compositions that are economical to produce.

These and other objectives and advantages of the present invention, some of which are specifically described and others that are not, will become apparent from the detailed description and claims that follow.

DETAILED DESCRIPTION OF THE INVENTION

The present invention relates to copolymers useful in the production of biocompatible polymeric compositions having a water content greater than 4.5 percent by weight to avoid water vacoule formation in vivo. Current commercial acrylic-based ophthalmic products having a water content less than 4.5 percent by weight have been known to trap water to form water vacoules or "glistenings" in vivo. The subject polymeric compositions having a higher water content greater than 4.5 percent by weight avoids problems related to water vacoule formation while achieving particularly desirable physical properties. The subject polymeric compositions have a relatively high refractive index of approximately 1.45 or greater and relatively high elongation of approximately 80 percent or greater. Accordingly, the subject polymeric compositions are ideal for use in the manufacture of ophthalmic devices.

Suitable copolymers for use in the production of the subject polymeric compositions are produced by combining two or more monomers selected from the group consisting of $C_{1-10}$ alkyl methacrylate such as for example but not limited to methyl methacrylate, butyl methacrylate or octyl methacrylate but preferably methyl methacrylate to control mechanical properties, $C_{1-10}$ alkyl acrylate such as for example ethyl acrylate, propyl acrylate or hexyl acrylate put preferably ethyl acrylate to control mechanical properties, $C_{6-40}$ arylalkyl acrylate such as for example but not limited to phenylpropyl acrylate or phenylbutyl acrylate but preferably phenylpropyl acrylate to increase refractive index, and $C_{6-40}$ arylalkyl methacrylate such as for example but not limited to phenylethyl methacrylate, phenylpentyl methacrylate or phenyloctyl methacrylate but preferably phenylethyl methacrylate to increase refractive index.

Examples of hydrophilic monomers useful for polymerization with one or more copolymers of the present invention include for example but are not limited to N,N-dimethylacrylamide, glycerol methacrylate, N-vinylpyrrolidinone and 2-hydroxyethyl methacrylate but preferably N,N-dimethylacrylamide for increased hydrophilicity.

One or more copolymers of the present invention along with one or more hydrophilic monomers may be polymerized alone or with one or more aromatic-based monomers, hydrophobic monomers or a combination thereof to produce polymeric compositions of the present invention.

Examples of aromatic-based monomers useful for polymerization with one or more copolymers and hydrophilic monomer(s) of the present invention include for example but are not limited to 2-phenyoxyethyl methacrylate, 3,3-diphenylpropyl methacrylate, 2-phenyloxyethyl methacrylate, 3-methacryloyloxypropyldiphenylmethylsilane, 2-(1-naphthylethyl) methacrylate, 3-phenylpropyl acrylate and 2-(2-naphthylethyl) methacrylate but preferably 2-(1-naphthylethyl) methacrylate for increased refractive index.

Examples of hydrophobic monomers useful for polymerization with one or more copolymers and hydrophilic monomer(s) of the present invention include for example but are not limited to 2-ethylhexyl methacrylate and methyl methacrylate and but preferably 2-ethylhexyl methacrylate for increased refractive index.

Polymeric compositions of the present invention are produced through free radical polymerization as illustrated below in Scheme 1.

Scheme 1

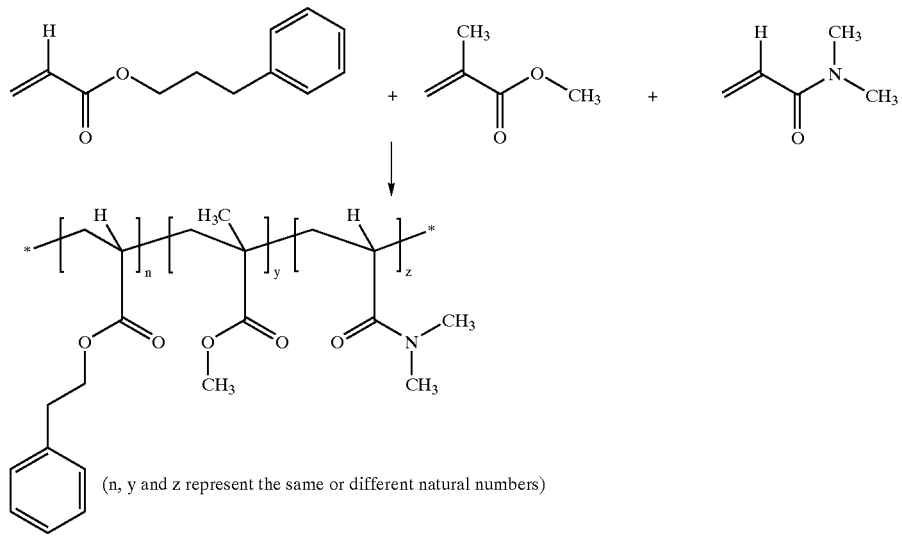

(n, y and z represent the same or different natural numbers)

The physical and mechanical properties of polymeric compositions produced from formulations based on the polymerization of the copolymer PPA/DMA/APDMS or (3-phenylpropyl acrylate-co-N,N-dimethylacrylamide-co-3-acryloyloxypropyldiphenylmethylsilane) are set forth below in Table 1.

TABLE 1

Mechanical and Physical Property Results of formulations based on copolymer PPA/DMA/APDMS

| Composition | W/W % | R.I. | Mod (g/mm$^2$) | Tear (g/mm) | % Elong. | % Rec. | % H$_2$O |
|---|---|---|---|---|---|---|---|
| PPA/DMA/APDMS/ hexanol/Eg* ** | 75/25/0/20/1 | 1.5349 | | | | | 5.1 |
| | 75/25/0/20/2 | 1.5364 | 55 | 24 | 197 | 88 | 6.5 |
| | 75/25/0/20/3 | | | | | 86 | 5.0 |
| | 65/25/10/20/1 | 1.5396 | 50 | 47 | 338 | 80 | 4.5 |
| | 65/25/10/20/2 | 1.5442 | 81 | 54 | 228 | 77 | 5 |
| | 65/25/10/20/3 | 1.5448 | 143 | 57 | 178 | 72 | 5.7 |

TABLE 1-continued

Mechanical and Physical Property Results of formulations based on copolymer PPA/DMA/APDMS

| Composition | W/W % | R.I. | Mod (g/mm²) | Tear (g/mm) | % Elong. | % Rec. | % H₂O |
|---|---|---|---|---|---|---|---|
| | 55/25/20/20/1 | 1.5409 | 94 | 79 | 332 | 70 | 5.5 |
| | 55/25/20/20/2 | 1.5429 | 141 | 77 | 232 | 64 | 4.8 |
| | 55/25/20/20/3 | 1.5422 | 196 | 83 | 184 | 60 | 5 |

*Eg = crosslinker ethyleneglycol dimethacrylate
**All formulations contain 0.5 percent by weight bis(2,4,6-trimethylbenzoyl)-phenylphosphine oxide, i.e., Irgacure ™ 819 (Ciba-Geigy, Basel, Switzerland) and no UV blocker The physical and mechanical properties of polymeric compositions of the present invention produced from formulations based on the copolymer PPA/DMA/MMA or (3-phenylpropyl acrylate-co-N,N-dimethylacrylamide-co-methyl methacrylate) are set forth below in Table 2.

TABLE 2

Mechanical and Physical Property Results of formulations based on the copolymer PPA/MMA/DMA

| Composition | W/W % | R.I. | Mod (g/mm²) | Tear (g/mm) | % Elong. | % Rec. | % H₂O |
|---|---|---|---|---|---|---|---|
| PPA/MMA/DMA* | 65/30/35 | 1.5108 | 290 | 127 | 254 | 30 | 11.3 |
| | 65/0/35 | 1.5252 | 81 | 16 | 89 | 95 | 6.7 |
| | 6510/35 | 1.5164 | 93 | 36 | 137 | 88 | 10.1 |
| | 6520/35 | 1.517 | 161 | 72 | 183 | 64 | 10.5 |

*Crosslinker ethyleneglycol dimethacrylate at 3.0%, initiator bis(2,4,6-trimethylbenzoyl)-phenylphosphine oxide, i.e., Irgacure ™ 819 at 0.5% and no UV blocker Low water content of greater than 4.5 percent but less than 15 percent water content by volume and high water content "hydrogels" of 15 percent or higher water content by volume polymeric compositions of the present invention having ideal physical characteristics for use in the manufacture of ophthalmic devices are described herein. In the production of such polymeric compositions of the present invention, one or more copolymers of the present invention are polymerized with one or more hydrophilic monomers to form crosslinked three-dimensional networks. However, one or more crosslinking agents may optionally be added in quantities less than 10 percent weight per volume (W/V) to the copolymers if desired prior to polymerization.

Examples of suitable crosslinking agents include but are not limited to diacrylates and dimethacrylates of triethylene glycol, butylene glycol, neopentyl glycol, hexane-1,6-diol, thio-diethylene glycol and ethylene glycol, trimethylolpropane triacrylate, N,N'-dihydroxyethylene bisacrylamide, diallyl phthalate, triallyl cyanurate, divinylbenzene; ethylene glycol divinyl ether, N,N-methylene-bis-(meth)acrylamide, sulfonated divinylbenzene and divinylsulfone.

Although not required, copolymers within the scope of the present invention may optionally have one or more strengthening agents added prior to polymerization preferably in quantities of less than about 80 weight percent but more typically from about 20 to about 60 weight percent.

Examples of suitable strengthening agents are described in U.S. Pat. Nos. 4,327,203, 4,355,147 and 5,270,418, each incorporated herein in its entirety by reference. Specific examples, not intended to be limiting, of such strengthening agents include cycloalkyl acrylates and methacrylates, such as for example tert-butylcyclohexyl methacrylate and isopropylcyclopentyl acrylate.

One or more ultraviolet light absorbers may optionally be added to the copolymers prior to polymerization in quantities typically less than 2 percent W/V. Suitable ultraviolet light absorbers for use in the present invention include for example but are not limited to β-(4-benzotriazoyl-3-hydroxyphenoxy)ethyl acrylate, 4-(2-acryloxyethoxy)-2-hydroxybenzophenone, 4-methacryloyloxy-2-hydroxybenzophenone, 2-(2'-methacryloyloxy-5'-methylphenyl)benzotriazole, 2-(2'-hydroxy-5'-methacryoxyethylphenyl)-2H-benzotriazole, 2-[3'-tert-butyl-2'-hydroxy-5'-(3"-methacryloyloxypropyl)phenyl]-5-chlorobenzotriazole, 2-(3'-tert-butyl-5'-(3"-dimethylvinylsilylpropoxy)-2'-hydroxyphenyl]-5-methoxybenzotriazole, 2-(3'-allyl-2'-hydroxy-5'-methylphenyl)benzotriazole, 2-[3'-tert-butyl-2'-hydroxy-5'-(3"-methacryloyloxypropoxy)phenyl]-5-methoxybenzotriazole, and 2-[3'-tert-butyl-2'-hydroxy-5'-(3"-methacyloyloxypropoxy)phenyl]-5-chlorobenzotriazole wherein β-(4-benzotriazoyl-3-hydroxyphenoxy)ethyl acrylate is the preferred ultraviolet light absorber.

One or more suitable free radical thermal polymerization initiators may be added to the copolymers of the present invention. Examples of such initiators include but are not limited to organic peroxides, such as acetyl peroxide, lauroyl peroxide, decanoyl peroxide, stearoyl peroxide, benzoyl peroxide, tert-butyl peroxypivalate, peroxydicarbonate, and the like. Preferably such an initiator is employed in a concentration of approximately 0.01 to 1 percent by weight of the total monomer mixture.

Representative ultraviolet light (UV) initiators include those known in the field such as for example but not limited to benzoin methyl ether, benzoin ethyl ether, Darocur™ 1173 (Bis(2,6-dimethoxybenzoyl)-2,4,4-trimethylpentylphosphine oxide), Darocur™ 1164 (CAS number 133108-07-3), Darocur™ 2273 (CAS number 104219-84-3), Darocur™ 1116 (1-propane, 2hydroxy-2-methyl-1-[4-(1-methylethyl)phenyl]), Darocur™ 2959 (4-(2-hydroxyethoxy)phenyl-(2-hydroxy-2-propyl) ketone), Darocur™ 3331 (photoinitiator with polymerizable group), Irgacur™ 651 (2,2-dimethoxy-2-phenylacetophenone) and Irgacur™ 184 (1-hydroxy cyclohexyl phenyl ketone) (Ciba-Geigy, Basel, Switzerland).

The polymeric compositions of the present invention are transparent, flexible, of relatively high refractive index and of relatively high elongation. The polymeric compositions of the present invention with the desirable physical properties noted above are particularly useful in the manufacture of ophthalmic devices such as but not limited to relatively thin, foldable intraocular lens implants, contact lenses and corneal inlays.

IOLs having relatively thin optic portions are critical in enabling a surgeon to minimize surgical incision size. Keeping the surgical incision size to a minimum reduces intraoperative trauma and postoperative complications. A relatively thin IOL optic portion is also critical for accommodating certain anatomical locations in the eye such as the anterior chamber and the ciliary sulcus. IOLs may be placed in the anterior chamber for increasing visual acuity in either aphakic or phakic eyes, or placed in the ciliary sulcus for increasing visual acuity in phakic eyes.

The polymeric compositions of the present invention have the flexibility required to allow implants manufactured from the same to be folded or deformed for insertion into an eye through the smallest possible surgical incision, i.e., 3.5 mm or smaller. It is unexpected that the subject polymeric compositions could possess the ideal physical properties described herein. The ideal physical properties of the subject polymeric compositions are unexpected because high refractive index copolymers typically lend to polymers that have increased crystallinity and decreased clarity, which does not hold true in the case of the subject polymeric compositions. The higher water content of greater than 4.5 percent by weight likewise reduces or eliminates water vacoule formation in vivo.

The subject copolymers and polymeric compositions produced therefrom are described in still greater detail in the examples that follow.

EXAMPLE 1

A film was cast using 65 parts phenylpropyl acrylate, 25 parts dimethylacrylamide, 10 parts methacryloyloxypropyl diphenylmethylsilane, 3 parts ethylene glycol dimethacrylate and 0.5 percent by weight bis(2,4,6-trimethylbenzoyl)-phenylphosphine oxide, i.e., Irgacure™ 819 photoinitiator. The cure conditions consisted of a two-hour ultraviolet irradiation. The films were then extracted in isopropanol for 24 hours, air dried and then hydrated in a borate buffered saline. The resultant films possessed a modulus of 143 g/mm$^2$, a tear strength of 57 g/mm and a water content of 5.7 percent by weight.

EXAMPLE 2

A film was cast using 65 parts phenylpropyl acrylate, 30 parts methyl methacrylate, 35 parts dimethylacrylamide, 3 parts ethylene glycol dimethacrylate and 0.5 percent by weight bis(2,4,6-trimethylbenzoyl)-phenylphosphine oxide, i.e., Irgacure 819 photoinitiator. The cure conditions consisted of a two-hour ultraviolet irradiation. The films were extracted in isopropanol for 24 hours, air dried and then hydrated in a borate buffered saline. The resultant films possessed a modulus of 290 g/mm$^2$, a tear strength of 127 g/mm and a water content of 11.3 percent by weight. The film was clear and showed no visible water vacoules after two months at 37° Celsius.

EXAMPLE 3

A film was cast using 65 parts phenylpropyl acrylate, 30 parts methyl methacrylate, 35 parts dimethylacrylamide, 3 parts ethylene glycol dimethacrylate and 0.5 percent by weight bis(2,4,6-trimethylbenzoyl)-phenylphosphine oxide, i.e., Irgacure 819 photoinitiator. The cure conditions consisted of a two-hour ultraviolet irradiation. The films were extracted in isopropanol for 24 hours, air dried and then hydrated in a borate buffered saline. The resultant films possessed a modulus of 761 g/mm$^2$, a tear strength of 340 g/mm and a water content of 3.7 percent by weight. The film was initially transparent following hydration, yet showed water vacuoles after two months at 37° Celsius.

Ophthalmic devices such as but not limited to IOLs manufactured using the polymeric compositions of the present invention can be of any design capable of being rolled or folded for implantation through a relatively small surgical incision, i.e., 3.5 mm or less. For example, ophthalmic devices such as IOLs typically comprise an optic portion and one or more haptic portions. The optic portion reflects light onto the retina and the permanently attached haptic portions hold the optic portion in proper alignment within an eye. The haptic portions may be integrally formed with the optic portion in a one-piece design or attached by staking, adhesives or other methods known to those skilled in the art in a multipiece design.

The subject ophthalmic devices, such as for example IOLs, may be manufactured to have an optic portion and haptic portions made of the same or differing materials. Preferably, in accordance with the present invention, both the optic portion and the haptic portions of the IOLs are made of one or more polymeric compositions of the present invention. Alternatively however, the IOL optic portion and haptic portions may be manufactured from differing materials and/or differing polymeric compositions of the present invention, such as described in U.S. Pat. Nos. 5,217,491 and 5,326,506, each incorporated herein in its entirety by reference. Once the particular material or materials are selected, the same is either cast in molds of the desired shape or cast in the form of rods and lathed or machined into disks. If cast in the form of rods and lathed or machined into disks, the disks are lathed or machined into IOLs at low temperatures below the glass transition temperature(s) of the material(s). The IOLs, whether molded or machined/lathed, are then cleaned, polished, packaged and sterilized by customary methods known to those skilled in the art.

In addition to IOLs, the polymeric compositions of the present invention are also suitable for use in the manufacture of other ophthalmic devices such as but not limited to contact lenses, keratoprostheses, capsular bag extension rings, corneal inlays, corneal rings or like devices.

IOLs manufactured using the unique polymeric compositions of the present invention are used as customary in the field of ophthalmology. For example, in a surgical procedure, an incision is placed in the cornea of an eye. Most commonly, through the corneal incision the natural lens of the eye is removed (aphakic application) such as in the case of a cataractous natural lens. An IOL is then inserted into the anterior chamber, posterior chamber or lens capsule of the eye prior to closing the incision. However, the subject ophthalmic devices may be used in accordance with other surgical procedures known to those skilled in the field of ophthalmology.

While there is shown and described herein copolymers, polymeric compositions, methods of producing the copolymers and polymeric compositions, methods of producing ophthalmic devices using the polymeric compositions and methods of using ophthalmic devices manufactured from the polymeric compositions, all in accordance with the present invention, it will be manifest to those skilled in the art that various modifications may be made without departing from the spirit and scope of the underlying inventive concept. The present invention is likewise not intended to be limited to particular devices described herein except insofar as indicated by the scope of the appended claims.

We claim:

1. Polymeric compositions comprising:
   one or more aromatic-based copolymers of two or more monomers at least one of which being aromatic, wherein said two or more monomers are selected from the group consisting of $C_{1-10}$ alkyl methacrylate, $C_{1-10}$ alkyl acrylate, $C_{6-40}$ arylalkyl acrylate and $C_{6-40}$ arylalkyl methacrylate polymerized with one or more hydrophilic monomers selected from the group consisting of N,N-dimethylacrylamide, glycerol methacrylate and N-vinylpyrrolidinone and optionally with one or more monomers selected from the group consisting of aromatic-based monomers and hydrophobic monomers, to have a water content greater than 4.5 percent by weight but less than 15 percent by weight, a refractive index of approximately 1.45 or greater and a elongation of approximately 80 percent or greater.

2. Polymeric compositions comprising:
   one or more aromatic-based copolymers of two or more monomers at least one of which being aromatic, wherein said two or more monomers are selected from the group consisting of $C_{1-10}$ alkyl methacrylate, $C_{1-10}$ alkyl acrylate, $C_{6-40}$ arylalkyl acrylate and $C_{6-40}$ arylalkyl methacrylate polymerized with one or more hydrophilic monomers selected from the group consisting of N,N-dimethylacrylamide, glycerol methacrylate and N-vinylpyrrolidinone and one or more aromatic-based monomers to have a water content greater than 4.5 percent by weight but less than 15 percent by weight, a refractive index of approximately 1.45 or greater and a elongation of approximately 80 percent or greater.

3. Polymeric compositions comprising:
   one or more aromatic-based copolymers of two or more monomers at least one of which being aromatic, wherein said two or more monomers are selected from the group consisting of $C_{1-10}$ alkyl methacrylate, $C_{1-10}$ alkyl acrylate, $C_{6-40}$ arylalkyl acrylate and $C_{6-40}$ arylalkyl methacrylate polymerized with one or more hydrophilic monomers selected from the group consisting of N,N-dimethylacrylamide, glycerol methacrylate and N-vinylpyrrolidinone and one or more hydrophobic monomers to have a water content greater than 4.5 percent by weight but less than 15 percent by weight, a refractive index of approximately 1.45 or greater and a elongation of approximately 80 percent or greater.

4. The polymeric compositions of claim 1 or 2 wherein said aromatic-based monomers are selected from the group consisting of 3,3-diphenylpropyl methacrylate, 2-phenyloxyethyl methacrylate, 3-methacryloyloxypropyldiphenylmethylsilane, 2-(1-naphthylethyl) methacrylate, 3-phenylpropyl acrylate and 2-(2-naphthylethyl) methacrylate.

5. The polymeric compositions of claim 1 or 3 wherein said hydrophobic monomers are selected from the group consisting of 2-ethylhexyl methacrylate and methyl methacrylate.

6. A method of producing the polymeric compositions of claim 1 comprising:
   producing one or more aromatic-based copolymers of two or more monomers at least one of which being aromatic, wherein said two or more monomers are selected from the group consisting of $C_{1-10}$ alkyl methacrylate, $C_{1-10}$ alkyl acrylate, $C_{6-40}$ arylalkyl acrylate and $C_{6-40}$ arylalkyl methacrylate, one or more hydrophilic monomers selected from the group consisting of N,N-dimethylacrylamide, glycerol methacrylate and N-vinylpyrrolidinone and optionally one or more monomers selected from the group consisting of aromatic-based monomers and hydrophobic monomers, to have a water content greater than 4.5 percent by weight but less than 15 percent by weight, a refractive index of approximately 1.45 or greater and a elongation of approximately 80 percent or greater.

7. A method of producing the polymeric compositions of claim 2 comprising:
   producing one or more aromatic-based copolymers of two or more monomers at least one of which being aromatic, wherein said two or more monomers are selected from the group consisting of $C_{1-10}$ alkyl methacrylate, $C_{1-10}$ alkyl acrylate, $C_{6-40}$ arylalkyl acrylate and $C_{6-40}$ arylalkyl methacrylate, one or more hydrophilic monomers selected from the group consisting of N,N-dimethylacrylamide, glycerol methacrylate and N-vinylpyrrolidinone and one or more aromatic-based monomers to have a water content greater than 4.5 percent by weight but less than 15 percent by weight, a refractive index of approximately 1.45 or greater and a elongation of approximately 80 percent or greater.

8. A method of producing the polymeric compositions of claim 3 comprising:
   producing one or more aromatic-based copolymers of two or more monomers at least one of which being aromatic, wherein said two or more monomers are selected from the group consisting of $C_{1-10}$ alkyl methacrylate, $C_{1-10}$ alkyl acrylate, $C_{6-40}$ arylalkyl acrylate and $C_{6-40}$ arylalkyl methacrylate, one or more hydrophilic monomers selected from the group consisting of N,N-dimethylacrylamide, glycerol methacrylate and N-vinylpyrrolidinone and one or more hydrophobic monomers to have a water content greater than 4.5 percent by weight but less than 15 percent by weight, a refractive index of approximately 1.45 or greater and a elongation of approximately 80 percent or greater.

9. The method of claim 6 or 7 wherein said aromatic-based monomers are selected from the group consisting of 3,3-diphenylpropyl methacrylate, 2-phenyloxyethyl methacrylate, 3-methacryloyloxypropyldiphenylmethylsilane, 2-(1-naphthylethyl) methacrylate, 3-phenylpropyl acrylate and 2-(2-naphthylethyl) methacrylate.

10. The method of claim 6 or 8 wherein said hydrophobic monomers are selected from the group consisting of 2-ethylhexyl methacrylate and methyl methacrylate.

11. A method of producing ophthalmic devices from the polymeric compositions of claim 1, 2 or 3 comprising:
    casting one or more polymeric compositions in the form of a rod;
    lathing or machining said rod into disks; and
    lathing or machining said disks into ophthalmic devices.

12. A method of producing ophthalmic devices from the polymeric compositions of claim 1, 2 or 3 comprising:
    pouring one or more polymeric compositions into a mold prior to curing;
    curing said one or more polymeric compositions; and
    removing said one or more polymeric compositions form said mold following curing thereof.

13. A method of using ophthalmic devices produced through the method of claim 11 comprising:
    implanting said ophthalmic device within the eye.

14. The method of claim 11 wherein said ophthalmic device is an intraocular lens.

15. The method of claim 11 wherein said ophthalmic device is a corneal inlay.

16. The polymeric compositions of claim 1, 2 or 3 wherein one or more strengthening agents are added prior to polymerization.

17. The polymeric compositions of claim 16 wherein said one or more strengthening agents are selected from the group consisting of cycloalkyl acrylates and methacrylates.

18. The polymeric compositions of claim 1, 2 or 3 wherein one or more crosslinking agents are added prior to polymerization.

19. The polymeric compositions of claim 18 wherein said one or more crosslinking agents are selected from the group consisting of diacrylates and dimethacrylates of triethylene glycol, butylene glycol, neopentyl glycol, hexane-1,6-diol, thio-diethylene glycol and ethylene glycol, trimethylolpropane triacrylate, N,N'-dihydroxyethylene bisacrylamide, diallyl phthalate, triallyl cyanurate, divinylbenzene; ethylene glycol divinyl ether, N,N-methylene-bis-(meth) acrylamide, sulfonated divinylbenzene and divinylsulfone.

20. The polymeric compositions of claim 1, 2 or 3 wherein one or more ultraviolet light absorbers are added prior to polymerization.

21. The polymeric compositions of claim 20 wherein said one or more ultraviolet light absorbers are selected from the group consisting of β-(4-benzotriazoyl-3-hydroxyphenoxy) ethyl acrylate, 4-(2-acryloxyethoxy)-2-hydroxybenzophenone, 4-methacryloyloxy-2-hydroxybenzophenone, 2-(2'-methacryloyloxy-5'-methylphenyl)benzotriazole, 2-(2'-hydroxy-5'-methacryoxyethylphenyl)-2H-benzotriazole, 2-[3'-tert-butyl-2'-hydroxy-5'-(3"-methacryloyloxypropyl)phenyl]-5-chlorobenzotriazole, 2-(3'-tert-butyl-5'-(3"-dimethylvinylsilylpropoxy)-2'-hydroxyphenyl]-5-methoxybenzotriazole, 2-(3'-allyl-2'-hydroxy-5'-methylphenyl)benzotriazole, 2-[3'-tert-butyl-2'-hydroxy-5'-(3"-methacryloyloxypropoxy)phenyl]-5-methoxybenzotriazole, and 2-[3'-tert-butyl-2'-hydroxy-5'-(3"-methacyloyloxypropoxy)phenyl]-5-chlorobenzotriazole.

22. The polymeric compositions of claim 1, 2 or 3 wherein one or more free radical thermal polymerization initiators are added prior to polymerization.

23. The polymeric compositions of claim 22 wherein said one or more free radical thermal polymerization initiators are selected from the group consisting of acetyl peroxide, lauroyl peroxide, decanoyl peroxide, stearoyl peroxide, benzoyl peroxide, tert-butyl peroxypivalate and peroxydicarbonate.

24. The polymeric compositions of claim 1, 2 or 3 wherein one or more ultraviolet light initiators are added prior to polymerization.

25. The polymeric compositions of claim 24 wherein said one or more ultraviolet light initiators are selected from the group consisting of benzoin methyl ether and benzoin ethyl ether.

26. A method of using ophthalmic devices produced through the method of claim 12 comprising:

implanting said ophthalmic device within the eye.

27. The method of claim 12 wherein said ophthalmic device is an intraocular lens.

28. The method of claim 13 wherein said ophthalmic device is an intraocular lens.

29. The method of claim 12 wherein said ophthalmic device is a corneal inlay.

30. The method of claim 13 wherein said ophthalmic device is a corneal inlay.

* * * * *

UNITED STATES PATENT AND TRADEMARK OFFICE
CERTIFICATE OF CORRECTION

PATENT NO.   : 6,852,793 B2
DATED        : February 8, 2005
INVENTOR(S)  : Joseph C. Salamone et al.

It is certified that error appears in the above-identified patent and that said Letters Patent is hereby corrected as shown below:

<u>Column 10,</u>
Line 27, replace "producing" with -- polymerizing --.
Line 63, replace "form" with -- from --.

Signed and Sealed this

Seventh Day of June, 2005

JON W. DUDAS
*Director of the United States Patent and Trademark Office*